United States Patent [19]

Oku et al.

[11] Patent Number: 5,354,759
[45] Date of Patent: Oct. 11, 1994

[54] ANGIOTENIN II ANTAGONIZING HETEROCYCLIC COMPOUNDS

[75] Inventors: Teruo Oku; Hiroyuki Setoi; Hiroshi Kayakiri; Shigeki Satoh; Takayuki Inoue; Yuki Sawada, all of Tsukuba; Akio Kuroda, Uji; Hirokazu Tanaka, Tsuchiura, all of Japan

[73] Assignee: Fujisawa Pharmaceutical Co., Ltd., Osaka, Japan

[21] Appl. No.: 8,646

[22] Filed: Jan. 25, 1993

Related U.S. Application Data

[63] Continuation-in-part of Ser. No. 758,688, Sep. 12, 1991, Pat. No. 5,215,994.

[30] Foreign Application Priority Data

Jan. 28, 1992 [GB] United Kingdom ............ 9201789.6

[51] Int. Cl.$^5$ ............... C07D 471/04; A61K 31/435
[52] U.S. Cl. ..................................... 514/303; 546/118
[58] Field of Search ...................... 546/118; 514/303

[56] References Cited

U.S. PATENT DOCUMENTS

| 5,057,522 | 10/1991 | Chen et al. | 546/118 |
| 5,215,994 | 6/1993 | Oku et al. | 546/118 |

FOREIGN PATENT DOCUMENTS

| 0400974 | 12/1990 | European Pat. Off. |
| 0426021 | 5/1991 | European Pat. Off. |
| 0459136 | 12/1991 | European Pat. Off. |
| 0480204 | 4/1992 | European Pat. Off. |
| 0510813 | 10/1992 | European Pat. Off. |
| 0518033 | 12/1992 | European Pat. Off. |

Primary Examiner—C. Warren Ivy
Assistant Examiner—Zinna N. Davis
Attorney, Agent, or Firm—Oblon, Spivak, McClelland, Maier & Neustadt

[57] ABSTRACT

This invention related to compounds of the formula

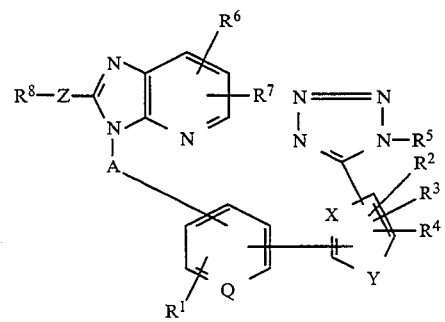

wherein the radicals are as defined in the claims. The compounds are angiotensin II antagonists useful in treating hypertension, etc.

14 Claims, No Drawings

ANGIOTENIN II ANTAGONIZING HETEROCYCLIC COMPOUNDS

This application is an continuation-in-part application of U.S. Ser. No. 07/758,688, filed Sep. 12, 1991, now U.S. Pat. No. 5,215,994.

The present invention relates to novel heterocyclic derivatives and a pharmaceutically acceptable salt thereof. More particularly, it relates to novel imidazole derivatives and a pharmaceutically acceptable salt thereof which have pharmaceutically activities such as angiotensin II antagonism and the like, to process for preparation thereof, to a pharmaceutical composition comprising the same and to a use of the same as a medicament.

Accordingly, one object of the present invention is to provide novel imidazole derivatives and a pharmaceutically acceptable salt thereof, which are useful as a potent and selective antagonist of angiotensin II receptor.

Another object of the present invention is to provide process for preparation of said imidazole derivatives or a salt thereof.

A further object of the present invention is to provide a pharmaceutical composition comprising, as an active ingredient, said imidazole derivatives or a pharmaceutically acceptable salt thereof.

Still further object of the present invention is to provide a use of said imidazole derivatives or a pharmaceutically acceptable salt thereof as a medicament such as angiotensin II antagonist useful for treating or preventing angiotensin II mediated diseases, for example, hypertension (e.g. essential hypertension, renal hypertension, etc.), heart failure, and the like in human being or animals.

The imidazole derivatives of the present invention are novel and can be represented by the formula (I):

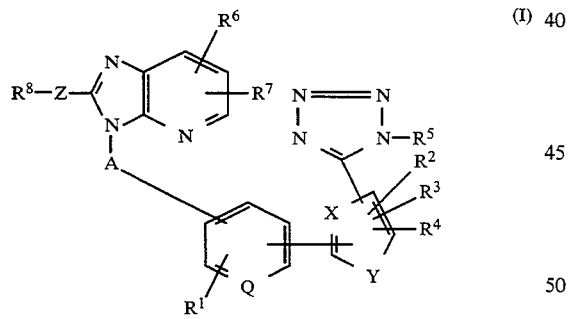

wherein
$R^1$ is hydrogen, halogen, nitro, lower alkyl, lower alkoxy, amino or acylamino,
$R^2$, $R^3$ and $R^4$ are each hydrogen, halogen, nitro, cyano, lower alkyl, lower alkenyl, lower alkylthio, mono or di or trihalo(lower)alkyl, oxo(lower)alkyl, hydroxy(lower)alkyl or optionally esterified carboxy; or
$R^2$ and $R^3$ are linked together to form 1,3-butadienylene,
$R^5$ is hydrogen or imino-protective group,
$R^6$ and $R^7$ are each hydrogen or lower alkyl,
$R^8$ hydrogen or lower alkyl which may have a substituent selected from the group consisting of halogen and lower alkoxy,
A is lower alkylene, Q is CH or N.

X is N or CH,

Y is NH, O or S, and

Z is NH, S, $SO_2$ or O.

According to the present invention, the object compound (I) can be prepared by the following processes.

Process 1

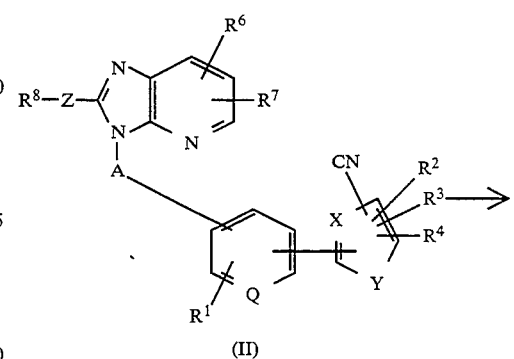

(II)

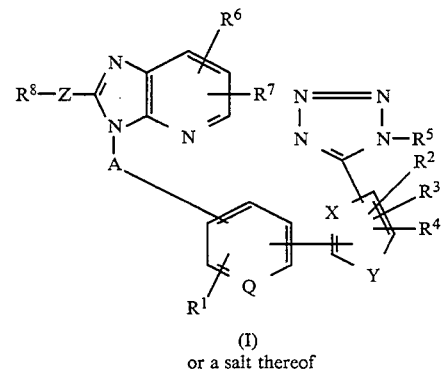

(I)
or a salt thereof

Process 2

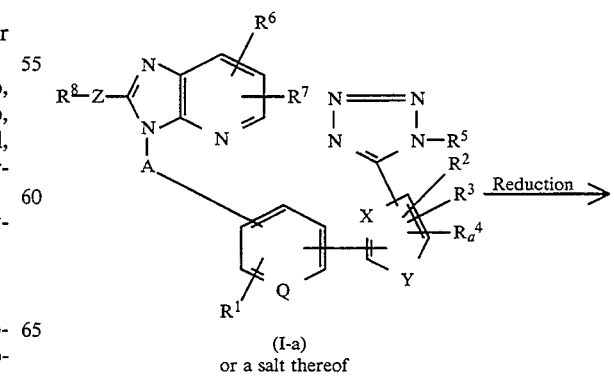

(I-a)
or a salt thereof

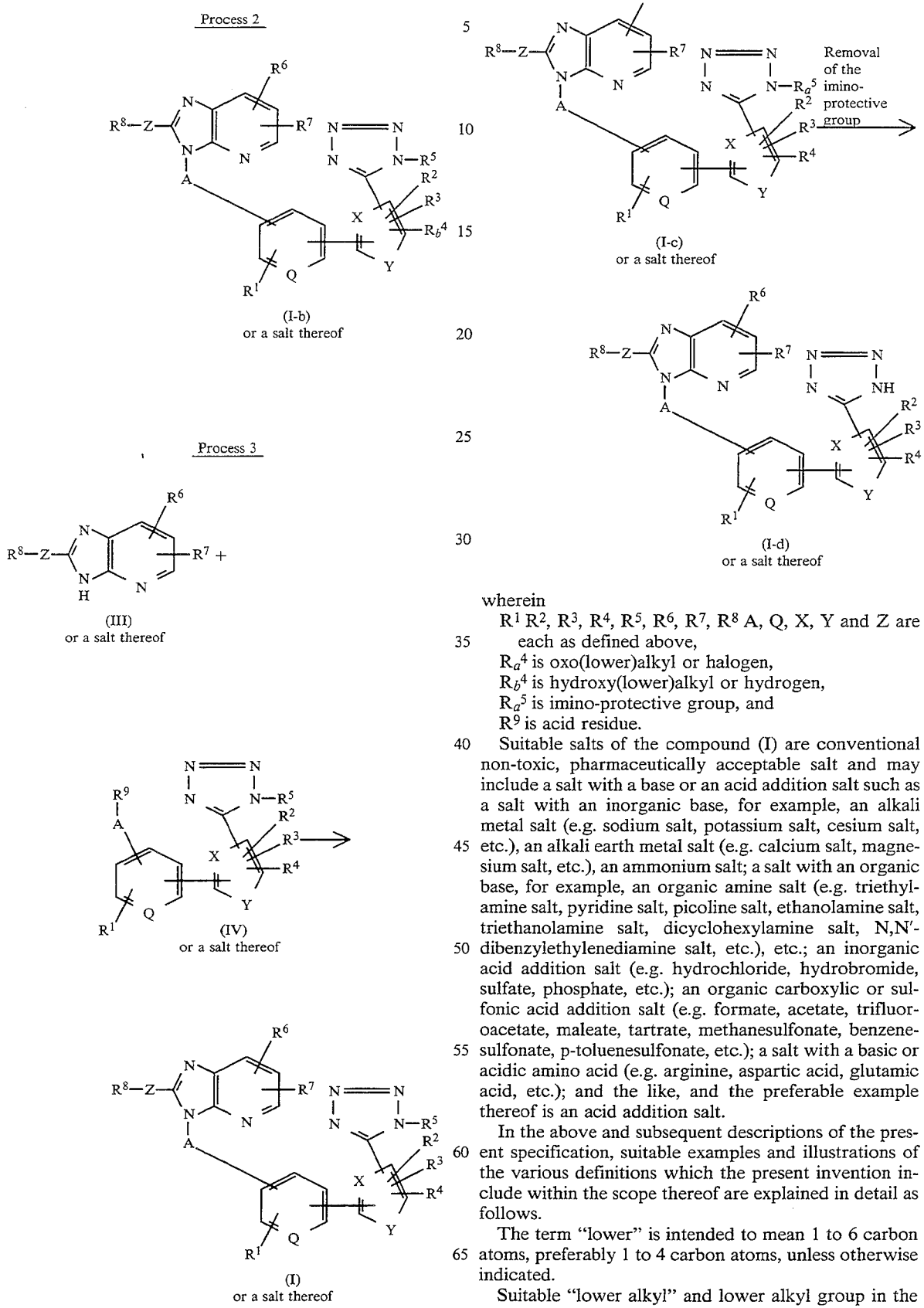

wherein
R[1] R[2], R[3], R[4], R[5], R[6], R[7], R[8] A, Q, X, Y and Z are each as defined above,
$R_a^4$ is oxo(lower)alkyl or halogen,
$R_b^4$ is hydroxy(lower)alkyl or hydrogen,
$R_a^5$ is imino-protective group, and
R[9] is acid residue.

Suitable salts of the compound (I) are conventional non-toxic, pharmaceutically acceptable salt and may include a salt with a base or an acid addition salt such as a salt with an inorganic base, for example, an alkali metal salt (e.g. sodium salt, potassium salt, cesium salt, etc.), an alkali earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N′-dibenzylethylenediamine salt, etc.), etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with a basic or acidic amino acid (e.g. arginine, aspartic acid, glutamic acid, etc.); and the like, and the preferable example thereof is an acid addition salt.

In the above and subsequent descriptions of the present specification, suitable examples and illustrations of the various definitions which the present invention include within the scope thereof are explained in detail as follows.

The term "lower" is intended to mean 1 to 6 carbon atoms, preferably 1 to 4 carbon atoms, unless otherwise indicated.

Suitable "lower alkyl" and lower alkyl group in the term "loweralkylthio" may include straight or branched one, having 1 to 6 carbon atom(s), such as methyl, ethyl, propyl, isopropyl, butyl, t-butyl, pentyl, hexyl, preferably one having 1 to 5 carbon atoms, and the like.

Suitable "lower alkenyl" may include vinyl, 1-propenyl, allyl, 1-butenyl, 2-pentenyl, and the like, preferably one having 2 to 4 carbon atoms, in which the most preferred one is vinyl.

Suitable "lower alkylene" is one having 1 to 6 carbon atom(s) and may include methylene, ethylene, trimethylene, propylene, tetramethylene, methyltrimethylene, dimethylethylene, hexamethylene, and the like, in which the preferred one is methylene.

Suitable "halogen" means fluoro, chloro, bromo and iodo.

Suitable "lower alkoxy" may include straight or branched one such as methoxy, ethoxy, propoxy, isopropoxy, butoxy, isobutoxy, tert-butoxy, pentyloxy, hexyloxy or the like, in which the preferable one is $C_1$-$C_4$ alkoxy.

Suitable acyl group in the term "acylamino" may include carbamoyl, thiocarbamoyl, sulfamoyl, aliphatic acyl, aromatic acyl, heterocyclic acyl, in which the preferable one is aliphatic acyl such as lower alkanoyl (e.g. formyl, acetyl, propionyl, hexanoyl, etc.).

Suitable "mono or di or trihalo(lower)alkyl" may include chloromethyl, fluoromethyl, difluoromethyl, dichloromethyl, trifluoromethyl, trifluoromethylpropyl, and the like.

Suitable "hydroxy(lower)alkyl" may include hydroxymethyl, hydroxyethyl, and the like.

Suitable "oxo(lower)alkyl" may include formyl, formylmethyl, formylethyl, and the like.

Suitable "esterified carboxy" may include lower alkoxycarbonyl (e.g. methoxycarbonyl, ethoxycarbonyl, etc.), and the like.

Suitable "imino-protective group" may include conventional one, and the preferable example thereof is ar(lower)alkyl such as mono-(or di- or tri-)phenyl(lower)alkyl (e.g. benzyl, benzhydryl, trityl, etc.), acyl such as lower alkoxycarbonyl (e.g. tert-butoxycarbonyl, etc.), lower alkanesulfonyl (e.g. mesyl, etc.), arenesulfonyl (e.g. tosyl, etc.), and the like, in which the most preferred one is trityl.

Suitable "acid residue" may include halogen (e.g. fluoro, chloro, bromo, iodo), acyloxy (e.g. acetoxy, tosyloxy, mesyloxy, etc.) and the like.

The preferred embodiment of the heterocyclic derivatives (I) of the present invention can be represented by the following chemical formula (I):

(I-1)

wherein
A is lower alkylene,
$R^2$, $R^3$ and $R^4$ are each hydrogen, halogen, nitro; or
$R^2$ and $R^3$ are linked together to form 1,3-butadienylene,
$R^6$ is lower alkyl,
$R^7$ and $R^8$ are each hydrogen or lower alkyl, and
Z is S, $SO_2$ or O,
in which lower alkyl, lower alkylene and halogen are each the same as those mentioned above.

Also, the preferred embodiment of the compound (I) can be represented by the following formula:

(I-2)

wherein
$R^1$ is hydrogen, halogen, nitro, lower alkoxy, amino or acylamino,
A is lower alkylene,
Q is CH or N,
$R^2$, $R^3$ and $R^4$ are each hydrogen, halogen, nitro; or
$R^2$ and $R^3$ are linked together to form 1,3-butadienylene,
$R^6$ is lower alkyl,
$R^7$ and $R^8$ are each hydrogen or lower alkyl, and
Z is S, $SO_2$ or O,
in which lower alkyl, halogen, lower alkoxy, acylamino and lower alkylene are each the same as those mentioned above.

Also, the preferred embodiment of the compound (I) can be represented by the following formula:

(I-3)

wherein
$R^1$ is hydrogen, halogen, nitro, lower alkyl, lower alkoxy, amino or acylamino,
$R^2$, $R^3$ and $R^4$ are each hydrogen, halogen, nitro, cyano, lower alkyl, or lower alkenyl; or
$R^2$ and $R^3$ are linked together to form 1,3-butadienylene,
$R^6$ is lower alkyl,
$R^7$ and $R^8$ are each hydrogen or lower alkyl,
A is lower alkylene,
Q is CH or N, and
Z is S, $SO_2$ or O, Also, the preferred embodiment of the compound (I) can be represented by the following formula:

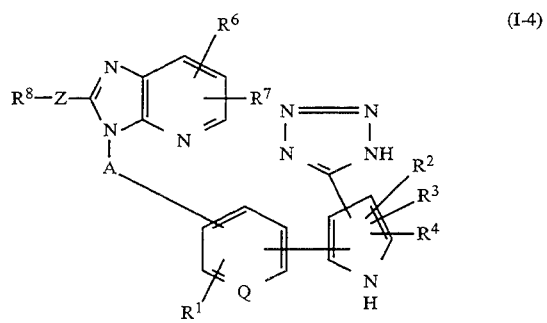
(I-4)

wherein
R¹ is hydrogen, halogen, nitro, lower alkyl, lower alkoxy, amino or acylamino,
R², R³ and R⁴ are each hydrogen, halogen, nitro, cyano, lower alkyl, lower alkenyl, lower alkylthio, mono or di or trihalo(lower)alkyl, oxo(lower)alkyl, hydroxy(lower)alkyl or optionally esterified carboxy; or
R² and R³ are linked together to form 1,3-butadienylene,
R⁶ and R⁷ are each hydrogen or lower alkyl,
R⁸ is hydrogen or lower alkyl which may have a substituent selected from the group consisting of halogen and lower alkoxy,
A is lower alkylene,
Q is CH or N, and
Z is NH, S, SO₂ or O,
in which each of these definitions is the same as those mentioned above.

Further, the preferred embodiment of the compound (I) can be represented by the following formula:

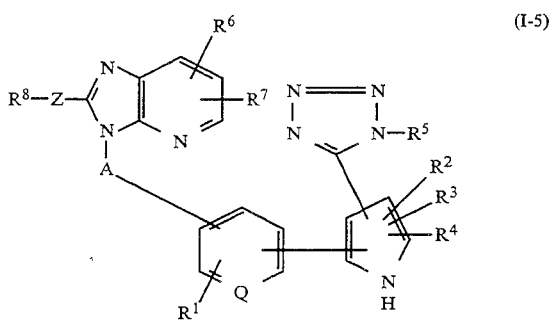
(I-5)

wherein
R¹ is hydrogen, halogen, nitro, lower alkyl, lower alkoxy, amino or acylamino,
R², R³ and R⁴ are each hydrogen, halogen, nitro, cyano, lower alkyl, lower alkenyl, lower alkylthio, mono or di or trihalo(lower)alkyl, oxo(lower)alkyl, hydroxy(lower)alkyl or optionally esterified carboxy; or
R² and R³ are linked together to form 1,3-butadienylene,
R⁵ is hydrogen or imino-protective group,
R⁶ and R⁷ are each hydrogen or lower alkyl,
R⁸ is hydrogen or lower alkyl which may have a substituent selected from the group consisting of halogen and lower alkoxy,
A is lower alkylene,
Q is CH or N, and
Z is NH, S, SO₂ or O,
in which each of these definitions is the same as those mentioned above.

Still further, the preferred embodiment of the compound (I) can be represented by the following formula:

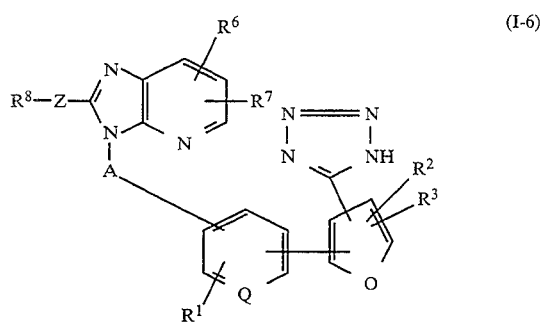
(I-6)

wherein
R¹ is hydrogen, halogen, nitro, lower alkyl, lower alkoxy, amino or acylamino,
R² and R³ are each hydrogen, halogen, nitro, cyano, lower alkyl, or lower alkenyl; or
R² and R³ are linked together to form 1,3-butadienylene,
R⁶ and R⁷ are each hydrogen or lower alkyl,
R⁸ is hydrogen or lower alkyl which may have a substituent selected from the group consisting of halogen and lower alkoxy,
A is lower alkylene,
Q is CH or N, and
Z is NH, S, SO₂ or O,
in which each of these definitions is each the same as those mentioned above.

Particularly, the preferred compound (I) of the present invention is represented by the following formula:

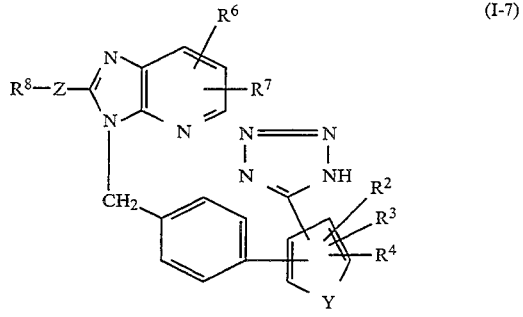
(I-7)

wherein
R², R³ and R⁴ are each hydrogen, halogen, nitro, cyano, lower alkyl, lower alkenyl, lower alkylthio, mono or di or trihalo(lower)alkyl, oxo(lower)alkyl, hydroxy(lower)alkyl or optionally esterified carboxy (more preferably carboxy or lower alkoxycarbonyl); or
R² and R³ are linked together to form 1,3-butadienylene,
R⁶ and R⁷ are each hydrogen or lower alkyl, R[8] is hydrogen or lower alkyl which may have a substituent selected from the group consisting of halogen and lower alkoxy, Y is NH, O, or S, and Z is NH, S, SO$_2$ or O, and further, more preferred embodiment of a group of the formula.

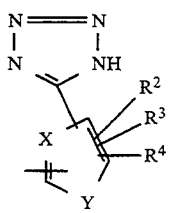

is represented by the following formula:

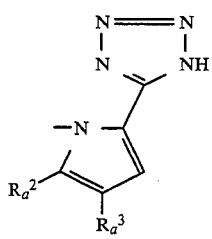  1)

wherein
R$_a^2$ is hydrogen, halogen, cyano, lower alkyl or lower alkylthio, and
R$_a^3$ is hydrogen, halogen, nitro, lower alkyl, lower alkenyl, trihalo(lower)alkyl, oxo(lower)alkyl, hydroxy(lower)alkyl or lower alkoxycarbonyl;

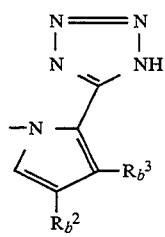  2)

wherein
R$_b^2$ and R$_b^3$ are each halogen;

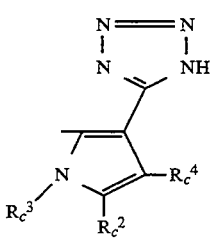  3)

wherein
R$_c^2$ is hydrogen, halogen or lower alkyl,
R$_c^3$ is lower alkyl, and
R$_c^4$ is hydrogen or halogen;

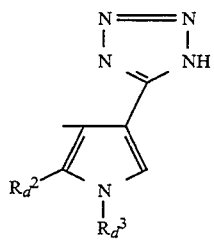  4)

wherein
R$_d^2$ is hydrogen, halogen or lower alkyl, and
R$_d^3$ is lower alkyl;

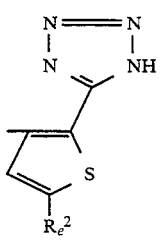  5)

wherein
R$_e^2$ is hydrogen or halogen; or

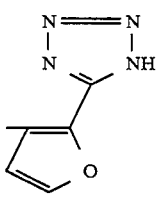  6)

and the most preferred one is:

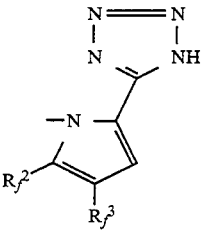

wherein R$_f^2$ and R$_f^3$ are each hydrogen, lower alkyl or halogen.

The processes for preparing the object compound (I) of the present invention are explained in detail in the following.

Process 1

The object compound (I) or a salt thereof can be prepared by subjecting the compound (II) to the formation reaction of a tetrazole group.

The agent to be used in the present reaction may include conventional ones which is capable of converting a cyano group to a tetrazolyl group such as metal azide, for example, alkali metal azide(e.g., potassium azide, sodium azide etc.), tri(lower)alkyltin azide(e.g. trimethyltin azide, etc.), triaryltin azide (e.g. triphenyltin azide, etc.), or the like.

The present reaction is usually carried out in the presence of a base such as tri(lower)alkylamine(e.g. triethylamine, etc.), and the like, or 1,3-dimethyl-2-imidazolidinone, and the like.

The present reaction is usually carried out in a solvent such as xylene, dioxane, chloroform, methylene chloride, 1,2-dichloroethane, tetrahydrofuran, pyridine, acetonitrile, dimethylformamide or any other solvent which does not adversely affect the reaction.

The reaction temperature is not critical and the reaction is usually carried out under warming or heating, preferably under heating.

Further, the compound (I) wherein $R^1$ is amino can be prepared by reducing the corresponding nitro compound in a conventional manner, and the compound (I) wherein $R^1$ is acylamino can be prepared by acylating the amino compound obtained above in a conventional manner.

And further, the present reaction includes, within its scope, the case that the dihalo(lower)alkyl group on $R^2$, $R^3$ or $R^4$ is transformed to the oxo(lower)alkyl group during the reaction or at the post-treating step of the present process.

Process 2

The object compound (I-b) or a salt thereof can be prepared by subjecting the compound (I-a) or a salt thereof to reduction.

The reduction may include, for example, chemical reduction with an alkali metal borohydride(e.g. sodium borohydride, etc.), and catalytic reduction with palladium catalysts (e.g. palladium on carbon, etc.), and the like.

This reaction is usually carried out in a conventional solvent which does not adversely influence the reaction such as alcohol [e.g. methanol, ethanol, propanol, etc.], tetrahydrofuran, dioxane, dimethylsulfoxide, N,N-dimethylformamide or a mixture thereof.

The reaction temperature is not critical, and the reaction is usually carried out under cooling to heating.

Process 3

The object compound (I) or a salt thereof can be prepared by reacting the compound (III) or a salt thereof with the compound (IV) or a salt thereof.

The present reaction is usually carried out in the presence of a base such as alkyl lithium (e.g. n-butyl lithium, etc.), alkali metal hydride (e.g. sodium hydride, potassium hydride, etc.), di(lower) alkylamine (e.g. diisopropylamine, etc.), tri(lower)alkylamine (e.g. trimethylamine, triethylamine, etc.), pyridine or its derivative (e.g. picoline, lutidine, 4-dimethylaminopyridine, etc.), or the like.

The present reaction is usually carried out in a solvent such as dioxane, dimethyl sulfoxide, dimethylformamide, diethylformamide, dimethylacetamide, benzene, tetrahydrofuran, or any other solvent which does not adversely affect the reaction. In case that the base to be used is liquid, it can also be used as a solvent.

The reaction temperature is not critical and the reaction is usually carried out under cooling, at ambient temperature or under heating.

Process 4

The object compound (I-d) or a salt thereof can be prepared by subjecting the compound (I-c) or a salt thereof to removal reaction of the imino-protective group.

Suitable method for this removal may include conventional one which is capable of removing an imino-protective group on a tetrazolyl group such as hydrolysis, reduction, or the like. The hydrolysis is preferably carried out in the presence of the base or an acid.

Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate, (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4,3,0]non-5-one, 1,4-diazabicyclo[2,2,-2]octane, 1,5-diazabicyclo[5,4,0]-ucdecene-5 or the like. The hydrolysis using a base is often carried out in water or a hydrophilic organic solvent or a mixed solvent thereof.

Suitable acid may include an organic acid (e.g. formic acid acetic acid, propionic acid, etc.) and an inorganic acid (e.g. hydrochloric acid, hydrobromic acid, sulfuric acid, etc.).

The present hydrolysis is usually carried out in an organic solvent, water or a mixed solvent thereof.

The reaction temperature is not critical, and the reaction is usually carried out at ambient temperature or under warming or heating.

The starting compounds (II), (III) and (IV) are new and can be prepared by the methods of Preparations mentioned below or a similar manner thereto or a conventional manner.

The object compound (I) of the present invention can be isolated and purified in a conventional manner, for example, extraction precipitation, fractional crystallization, recrystallization, chromtography, and the like.

The object compound (I) thus obtained can be converted to its salt by a conventional method.

The object compound (I) of the present invention exhibits angiotensin antagonism such as vasodilating activity and is useful as an angiotensin II antagonist and effective to various angiotensin II mediated diseases such as hypertension (e.g. essential hypertension, renal hypertension, etc.), heart failure, and the like.

Further, the object compounds of the present invention are useful as therapeutical and/or preventive agents for cardiopathy (e.g. angina pectoris, arrhythmia, myocardial infarction, etc.), hyperaldosteronism, cerebral vascular diseases, senile dementia, ophtahlimic diseases (e.g. glaucoma, etc.), and the like; and diagnostic agents to test the renin angiotensin system.

For therapeutic or preventive administration, the object compound(I) of the present invention are used in the form of conventional pharmaceutical preparation which contains said compound as an active ingredient, in admixture with pharmaceutically acceptable carriers such as an organic or inorganic solid or liquid excipient which is suitable for oral, parenteral, external and inhalant administration. The pharmaceutical preparation may be in solid form such as tablet, granule, powder, capsule, or liquid form such as solution, suspension, syrup, emulsion, lemonade and the like.

If needed, there may be included in the above preparations auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound (I) may vary from and also depend upon the age, conditions of the patient, a kind of diseases or conditions, a kind of the compound (I) to be applied, etc. In general amounts between 0.01 mg and about 500 mg or even more per day may be administered to a patient. An average single dose of about 0.05 mg, 0.1 mg, 0.25 mg, 0.5 mg, 1 mg, 20 mg, 50 mg, 100 mg of the object compound (I) of the present invention may be used in treating diseases.

The following Preparations and Examples are given for the purpose of illustrating the present invention.

Preparation 1

To a solution of 2-ethylthio-7-methyl-3H-imidazo[4,5-b]pyridine (1.50 g) in dimethylformamide (15 ml) was added sodium hydride (341 mg) at room temperature under nitrogen atmosphere. The mixture was stirred for 30 minutes at the same room temperature under nitrogen atmosphere. To the mixture was added a solution of 1-(4-bromomethylphenyl)-4-chloropyrrole-2-carbonitrile (2.19 g) in dimethylformamide (15 ml). The mixture was stirred for 3 hours at room temperature. The mixture was treated with aqueous sodium bicarbonate solution, extracted twice with ethyl acetate. The extracts were washed with water, dried over magnesium sulfate, and evaporated. The residue was purified by silica gel column chromatography (eluted by n-hexane/ethyl acetate=1/1) to yield 2-ethylthio-3-[4-(4-chloro-2-cyano-1-pyrrolyl)benzyl]-7-methyl-3H-imidazo-[4,5-b]pyridine (850 mg) as a yellow oil.

NMR (CDCl$_3$,δ): 1.46(3H, t, J=7.5 Hz), 2.64(3H, s), 3.41(2H, q, J=7.5 Hz), 5.44(2H, s), 6.89(1H, d, J=2 Hz), 6.96-7.04(2H, m), 7.35(2H, d, J=9 Hz), 7.46(2H, d, J=9 Hz), 8.14(1H, d, J=5 Hz)

Preparation 2

To a stirred solution of 2-ethylthio-7-methyl-3H-imidazo[4,5-b]-pyridine (3.00 g) in dimethylformamide (30 ml) was added sodium hydride (60%:627 mg) portionwise under ice-cooling below 10° C. under nitrogen atmosphere. A solution of 3-(4-bromomethylphenyl)-2-bromopyrrole-4-carbonitrile (5.50 g) in dimethylformamide (50 ml) was added to the reaction mixture at the same temperature under nitrogen atmosphere. The mixture was stirred for 3 hours at ambient temperature. The resulting mixture was extracted twice with ethyl acetate. The extracts were washed with water, dried, and evaporated under reduced pressure. The residue was purified by flash column chromatography on silica gel eluted by a mixture of ethyl acetate and n-hexane (1:1) to yield 3-[4-(2-bromo-4-cyano-1-methyl-2-pyrrolyl)-benzyl]-2-ethylthio-7-methyl-3H-imidazo[4,5-b]-pyridine (1.32 g) as white powder. mp: 161°–163° C.

NMR (CDCl$_3$, δ): 1.45(3H, t, J=7.5 Hz), 2.65(3H, s), 3.39(2H, q, J=7.5 Hz), 3.68(3H, s), 5.43(2H, s), 6.99(1H, d, J=5 Hz), 7.30(1H, s), 7.37(2H, d, J=9 Hz), 7.48(2H, d, J=9 Hz), 8.15(1H, d, J=5 Hz),

Preparation 3

To a solution of 2-ethylthio-7-methyl-3H-imidazo[4,5-b]pyridine (3.00 g) in dimethylformamide (30 ml) was added sodium hydride (627 mg) portionwise at room temperature under nitrogen atmosphere. The mixture was stirred at room temperature for an hour. To the mixture was added a solution of 1-ethyl-2-(4-methanesulfonyloxymethyl phenyl)-5-methylpyrrole-2-carbonitrile (4.94 g) in dimethylformamide (50 ml). The reaction mixture was stirred at room temperature for 3 hours. Water was added therein, and extracted twice with ethyl acetate. The extracts were washed with water, dried over magnesium sulfate, and concentrated. The residue was purified by flash column chromatography eluted by n-hexane/ethyl acetate (1/1) to give 3-[4-(3-cyano-1-ethyl-5-methyl-2-pyrrolyl)benzyl]-2-ethylthio-7-methyl-3H-imidazo[4,5-b]pyridine (1.52 g) as colorless oil.

NMR (CDCl$_3$, δ): 1.26(3H, t, J=7.5 Hz), 1.45(3H, t, J=7.5 Hz), 2.29(3H, s), 2.65(3H, s), 3.40(2H, q, J=7.5 Hz), 3.81(2H, q, J=7.5 Hz), 5.46(2H, s), 6.20(1H, s), 7.00(1H, d, J=5 Hz), 7.33(2H, d, J=9 Hz), 7.40(2H, d, J=9 Hz), 8.16(1H, d, J=5 Hz)

Preparation 4

A mixture of 2-amino-4-methyl-3-nitropyridine (25.0 g) and N,N-dimethylaniline (50 ml) was heated to 70° C., to the solution was added dropwise acetyl chloride (12.2 ml) and the mixture was stirred at the same temperature for an hour. The reaction mixture was extracted with ethyl acetate. The extract was washed with water(three times) and brine. The solution was dried over magnesium sulfate and the solvent was evaporated in vacuo. The residue was dissolved in methanol (200 ml) and saturated aqueous sodium bicarbonate solution (50 ml) was added therein. The mixture was stirred at 70° C. for 30 minutes. After being cooled to room temperature, the solvent was evaporated. The residue was extracted with ethyl acetate. The extract was washed with water. Aqueous layer was neutralized with 1N hydrochoric acid, and extracted with ethyl acetate. The combined organic layer was washed saturated aqueous sodium chloride and dried over magnesium sulfate. Resulting crude crystal was suspended in isopropyl ether (200 ml) and the mixture was heated to 90° C. After the mixture was allowed to cool to room temperature, and the solid was collected by filtration and air-dried at room temperature, to give 2-acetylamino-4-methyl-2-nitropyridine (25.99 g) as pale yellow needle. The filtrate was condensed in vacuo to give the second crop (1.31 g). mp: 146°–149° C.

NMR (CDCl$_3$, δ): 2.30(3H, s), 2.51(3H, s), 7.12(1H, d, J=5 Hz), 8.39(1H, d, J=5 Hz), 8.45(1H, br, s)

Preparation 5

To a solution of sodium hydride (3.2 g) in dimethylformamide (100 ml) was added 2-acetylamino-4-methyl-2-nitropyridine (15.21 g) portionwise below 40° C. and the mixture was stirred at room temperature for 30 minutes, and a solution of 1-(4-methanesulfonyloxymethylphenyl)-5-methyl-2-carbonitrile (22.65 g) in dimethylformamide (120 ml) was added dropwise therein. The reaction mixture was stirred at room temperature for 1.5 hours. The mixture was quenched with ice and added saturated acqueous sodium bicarbonate. The mixture was extracted with ethyl acetate, the organic layer was separated, and washed with brine. The acqueous layer was extracted with ethy acetate. The combined ethyl acetate layer was dried over magnesium sulfate, and concentrated in vacuo. The residue was purified by flash column chromatography (by n-hexane/ethyl acetate=2/1→½) to yield 2-[N-acetyl-4-[1-(2-cyano-5-methyl)pyrrolyl]benzyl]amino-4-methyl-3-nitropyridine (22.65 g) as a brown viscous oil.

NMR (CDCl$_3$, δ): 1.99(3H, s), 2.15(3H, s), 2.44(3H, s), 4.75-5.33(2H, m), 6.08(1H, d, J=5 Hz), 6.86(1H, d, J=5 Hz), 7.06-7.76(5H, m), 8.50(1H, d, J=5 Hz)

Preparation 6

To a stirred solution of 2-[N-acetyl-4-[1-(2-cyano-5-methylpyrrolyl)benzyl)]-4-methyl-3-nitropyridine(20.34 g) in methanol (500 ml) was added sodium methoxide in methahol solution(28% w/v; 50 ml) at ambient temperature. The mixture was stirred at the same temperature for one hour and then diluted with ether. The aqueous phase was extracted with ether and combined ether phase was washed with water, saturated sodium chloride and dried over magnesium sulfate. After filtration, the organic phase was concentrated in vacuo. The residue was chromatographed on silica gel eluting with dichloromethane-n-hexane(3:1 then 4:1) to give 2-[4-[1-(2-cyano-5-methyl)pyrrolyl]-benzyl]amino-4-methyl-3-nitropyridine as a yellow solid. Recrystallization gave yellow prism (17.18 g). mp: 102°-103° C.

NMR (CDCl$_3$, δ): 2.14(3H, s), 2.57(3H, s), 4.86(2H, d, J=8 Hz), 6.05(1H, d, J=4 Hz), 6.58(1H, d, J=5 Hz), 6.84(1H, d, J=4 Hz), 7.28(2H, d, J=9 Hz), 7.47(2H, d, J=9Hz), 7.88(1H, br, s), 8.16(1H, d, J=5 Hz)

Preparation 7

A mixture of 2-[4-[1-(2-cyano-5-methyl)pyrrolyl]benzyl]amino-4-methyl-3-nitropyridine (500 g), 10% palladium on carbon(50 mg) and ethanol (10 ml) was stirred at room temperature for 5 hours under hydrogen atmosphere (1 atm). To the mixture was added 1,4-dioxane at the same temperature under stirring under hydrogen atmosphere (1 atm). After 3 hours, to the mixture was added addition of 10% palladium on carbon (100 mg), and stirred at the same temperature for 105 minutes under hydrogen atmosphere (1 atm). Ethanol was added to the mixture and the mixture was filtered through celite and the filtrate was evaporated in vacuo to give crude products of 3-amino-2-[4-[1-(2-cyano-5-methylpyrrolyl)benzyl]amino]-4-methylpyridine (537 mg) which was used for the next reaction without further purification.

Preparation 8

A mixture of 3-amino-2-[4-[1-(2-cyano-5-methyl-pyrrolyl)benzyl]amino]-4-methylpyridine (530 mg) and tetraethylorthocarbonate (331 ul) in acetic acid (5 ml) was stirred at ambient temperature for four and half an hour. After another of tetraethyl orthocarbonate(331 ul) was added, the mixture was stirred at ambient temperature for one hour and then at 70° C. for two hours. The solvent was removed in vacuo and the residue was extracted with saturated sodium bicarbonate, water (twice), and saturated sodium chloride and dried over magmesium sulfate. After filtration, the solvent was removed in vacuo and the residue was purified by silica gel column chromatography eluting with ethyl acetate-n-hexene (1:3 then 1:1) to afford 3-[4-[1-(2-cyano-5-methyl)pyrrolyl]-benzyl]-2-ethoxy-7-methyl-3H-imidazo[4,5-b]pyridine (429 mg) as a pinky amorphous solid.

NMR (CDCl$_3$, δ): 1.47(3H, t, J=7.5 Hz), 2.10(3H, s), 2.56(3H, s), 4.65(2H, q, J=7.5 Hz), 5.32(2H, s), 6.04(1H, d, J=4 Hz), 6.85(1H, d, J=4 Hz), 6.95(1H, d, J=5 Hz), 7.22(2H, d, J=9 Hz), 7.45(2H, d, J=9 Hz), 8.06(1H, d, J=5 Hz)

Preparation 9

A mixture of 2-amino-4,6-dimethyl-3-nitropyridine (14.91 g) and N,N-dimethylaniline (80 ml) was heated at 70° C. To the solution was added dropwise acetyl chloride at 70° C. and the mixture was stirred at 70° C. for 2.5 hours. To the reaction mixture was added ethyl acetate(500 ml). The organic layer was separated. and washed with water three times and brine. The solution was dried over magnesium sulfate and the solvent was evaporated in vacuo. The residue was dissolved in hot isopropyl ether (200 ml), and cooled to ambient temperature. After the mixture was cooled in an ice bath for an hour, the resulting solid collected by filtration, was washed with cold isopropyl ether, purified by flash column chromatography on silica gel eluted by a mixture of ethyl acetate and n-hexane (1:9 then 2:1) to yield a brown oil and the oil was dissolved methanol(40 ml). To the solution was added saturated sodium bicarbonate (10 ml), and stirred at room temperature for 70 minutes. The mixture was diluted with ethy acetate, organic layer was separated, and the aqueous layer was extracted with ethy acetate. The combined ethyl acetate layer was washed with water, dried over magnesium sulfate, and concentrated in vacuo. To the residue was added diisopropyl ether (50 ml). After cooling, the solid was collected by filtration and washed diisopropyl ether to give 2-acetylamino-4,6-dimethyl-3-nitropyridine(5.56 g) as colorless powder.

NMR (CDCl$_3$, δ): 2.28(3H, s), 2.44(3H, s), 2.50(3H, s), 6.94(1H, s), 8.30 (1H, br, s)

Preparation 10

To a solution of 2-acetylamino-4,6-dimethyl-2-nitropyridine (330 mg) in dimethylformamide (3 ml) was added sodium hydride (64 mg) at room temperature. The mixture was stirred at room temperature for 30 minutes, and a solution of 1-(4-methanesulfonyloxymethylphenyl)-1-ethyl-5-methyl-2-carbonitrile (500 mg) in dimethylformamide (6 ml) was added dropwise therein. The reaction mixture was stirred at room temperature for 30 minutes. The mixture quenched with saturated ammonium chloride, and was extracted with ethyl acetate. The extract was washed with water and brine, and dried over magnesium sulfate, and concentrated in vacuo. The residue was purified by flash column chromatography (elution by ethyl acetate/n-hexane=1/1→2/1) to yield 2-[N-acetyl-4-[2-(3-cyano-1-ethyl-5-methyl)pyrrolyl]benzyl]amino-4,6-dimethyl-3-nitropyridine (514 mg) as a brown viscous oil.

NMR (CDCl$_3$, δ): 1.17(3H, t, J=7.5 Hz), 1.97(3H, br, s), 2.25(3H, s), 2.33(br, s, 3H), 2.53(3, H, s), 3.84(2H, q, J=7.5 Hz), 4.73-5.36(2H, m), 6.19(1H, s), 7.04-7.86(5H, m)

Preparation 11

The following compound was obtained according to a similar manner to that of preparation 6.

2-[4-[2-(3-cyano-1-ethyl-5-methyl)pyrrolyl]benzyl]amino-4,6-dimethyl-3nitropyridine. mp: 122°-126° C.

NMR (CDCl$_3$, δ): 1.20(3H, t, J=7.5 Hz), 2.30(3H, s), 2.40(3H, s), 2.55(3H, s), 3.86(2H, q, J=7.5 Hz), 4.87(2H, d, J=5 Hz), 6.21(1H, s), 6.40(1H, s), 7.37(2H, d, J=9 Hz), 7.46(2H, d, J=9 Hz), 8.21 (1H, br, t, J=5 Hz)

Preparation 12

The following compound was obtained according to a similar manner to that of preparation 7, and the compound was used for the next reaction without further purification.

3-Amino-2-[4-[2-(3-cyano-1-ethyl-5-methyl)pyrrolyl]benzyl]amino-4,6-dimethylpyridine.

Preparation 13

The following compound was obtained according to a similar manner to that of preparation 8.

3-[4-[2-(3-Cyano-1-ethyl-5-methyl)pyrrolyl]benzyl]-5,7-dimethyl-2-ethoxy-3H-imidazo[4,5-b]pyridine.

NMR (CDCl$_3$, δ): 1.15(3H, t, J=7.5 Hz), 1.42(3H, t, J=7.5 Hz), 2.29(3H, s, 2.50(3H, s), 2.56(3H, s), 3.83(2H, q, J=7.5 Hz), 4.61(2H, q, J=7.5 Hz), 5.28(2H, s), 6.20(1H, s), 6.82(1H, s), 7.31(2H, d, J=9 Hz), 7.41 (2H, d, J=9 Hz)

Preparation 14

A mixture of 3-amino-2-[4-[2-(3-cyano-1-ethyl-5-methyl)-pyrrolyl]benzyl]amino-4,6-dimethylpyridine (0.50 mmol) and 1,1'-carbonyldiimidazole(97 mg) was stirred at ambient temperatuve for half an hour and then heated under reflux for 12 hours during which time another of 1,1'-carbonyldiimidazole (65 mg) was added. After cooling, the mixture was extracted with ethyl acetate and washed with 1N hydrochloric acid, water and saturated sodium chloride. After being dried over magnesium sulfate, the solvent was evaporated in vacuo and the residue was recrystallized from ethanol to give 3-[4-[2-(3-cyano-1-ethyl-5-methyl)pyrrolyl]benzyl]-5,7-dimethyl-2-hydroxy-3H-imidazo[4,5-b]pyridine (120 mg) as pale orange powder. mp: 281°–286° C.

NMR (CDCl$_3$, δ): 1.15(3H, t, J=7.5 Hz), 2.27(3H, s), 2.34(3H, s), 2.50(3H, s), 3.32(2H, q, J=7.5 Hz), 5.20(2H, s), 6.19(1H, s), 6.70(1H, s), 7.31(2H, d, J=9 Hz), 7.56(2H, d, J=9 Hz), 9.85(1H, s)

Preparation 15

A suspension of 3-[4-[2-(3-cyano-1-ethyl-5-methyl)-pyrrolyl]-benzyl]-5,7-dimethyl-2-hydroxy-3H-imidazo[4,5-b]pyridine(120 mg) and N,N-dimethylaniline (80 μl) in phosphoryl oxychloride (0.9 ml) was heated under reflux for two and half an hour. The solvent was removed in vacuo and the residual solvent was evaporated azeotropically with toluene. The residue was extracted with ethyl acetate and washed with saturated sodium bicorbonate and satured sodium chloride. The organic layer was dried over magnesium sulfate, filterd and concentratedin vacuo to afford 2-chloro-3-[4-[2-(3-cyano-1-ethyl-5-methyl)pyrrolyl]benzyl]-5,7-dimethyl-3H-imidazo[4,5-b]pyridine as a yellow amorphous solid.

NMR (CDCl$_3$, δ): 1.17(3H, t, J=7.5 Hz), 2.28(3H, s), 2.60(3H, s), 2.64(3H, s), 3.82(2H, q, J=7.5 Hz), 5.51(2H, s), 6.20(1H, s), 6.97(1H, s), 7.36(2H, d, J=9 Hz), 7.43(2H, d, J=9 Hz)

Preparation 16

To a suspension of 2-chloro-3-[4-[2-(3-cyano-1-ethyl-5-methyl)-pyrrolyl]benzyl]-5,7-dimethyl-3H-imidazo[4,5-b]pyridine (120 mg) in methanol (1 ml) was added sodium methoxide (28% w/v in methanol; 0.57 ml) and tetrahydrofuran (1 ml) at ambient temperature. After the mixture became clear solution, it was heated at 50° C. for 7 hours. The mixture was diluted with ethyl acetate and washed with saturated sodium bicarborate and saturated sodium chloride. The organic phase was dried over magnesium sulfate, filtered and evaporated in vacuo to afford 3-[4-[2-(3-cyano-1-ethyl-5-methyl)pyrrolyl]benzyl]-5,7-dimethyl-2-methoxy-3H-imidazo[4,5-b]pyridine as a pale brown viscous oil (101 mg).

NMR (CDCl$_3$, δ): 1.16(3H, t, J=7.5 Hz), 2.27(3H, s), 2.53(3H, s), 2.59(3H, s), 3.33(2H, q, J=7.5 Hz), 4.20(3H, s), 5.29(2H, s), 6.20(1H, s), 6.83(1H, s), 7.33(2H, d, J=9 Hz), 7.40(2H, d, J=9 Hz)

Preparation 17

The following compound was obtained according to a similar manner to that of preparation 16.

3-[4-[2-(3-Cyano-1-ethyl-2-methyl)pyrrolyl]benzyl]-5,7-dimethyl-2-propoxy-3H-imidazo[4,5-b]pyridine. colorless powder mp: 133°–137° C.

NMR (CDCl$_3$, δ): 0.97(3H, t, J=7.5 Hz), 1.15(3H, t, J=7.5 Hz), 1.81(2H, m), 2.26(3H, s), 2.50(3H, s), 2.57(3H, s), 3.82(2H, q, J=7.5 Hz), 4.50(2H, t, J=8 Hz), 5.39(2H, s), 6.20(1H, s), 6.80(1H, s), 7.32(2H, d, J=9 Hz), 7.41(2H, d, J=9 Hz)

Preparation 18

The following compound was obtained according to a similar manner to that of preparation 16.

3-[4-[2-(3-Cyano-1-ethyl-5-methyl)pyrrolyl]benzyl]-5,7-dimethyl-2-(2,2,2-trifluoro)ethoxy-3H-imidazo[4,5-b]pyridine. pale brown powder mp: 144°–147° C.

NMR (CDCl$_3$, δ): 1.14(3H, t, J=7.51 Hz), 2.26(3H, s), 2.50(3H, s), 2.59(3H, s), 3.81(2H, q, J=7.5 Hz), 4.95(2H, q, J=8 Hz), 5.31(2H, s), 6.19(1H, s), 6.86(1H, s), 7.35(2H, d, J=9 Hz), 7.46(2H, d, J=9 Hz)

Preparation 19

The following compound was obtained according to a similar manner to that of preparation 16.

3-[4-[2-(3-Cyano-1-ethyl-5-methyl)pyrrolyl]benzyl]-5,7-dimethyl-2-(2-methoxyethoxy)-3H-imidazo[4,5-b]pyridine. pale redish brown solid mp: 129°–138° C.

NMR (CDCl$_3$, δ): 1.16(3H, t, J=7.5 Hz), 2.27(3H, s), 2.51(3H, s), 2.57(3H, s), 3.39(3H, s), 3,72–3.80(2H, m), 3.82(2H, q, J=7.5 Hz), 4.67–4.76(2H, m) 5.31(2H, s), 6.20(1H, s), 6.81(1H, s), 7.32(2H, d, J=8.5 Hz), 7.46(2H, d, J=8.5 Hz)

Preparation 20

The following compound was obtained according to a similar manner to that of preparation 16.

3-[4-[2-(3-Cyano-1-ethyl-5-methyl)pyrrolyl]benzyl]-5,7-dimethyl-2-isopropoxy-3H-imidazo[4,5-b]pyridine. white solid mp: 158°–159.5° C.

NMR (CDCl$_3$, δ): 1.14(3H, t, J=7.5 Hz), 1.37(3H, s), 1.40(3H, s), 2.27(3H, s), 2.50(3H, s), 2.56(3H, s), 3.82(2H, q, J=7.5 Hz), 5.26(2H, s), 5.42(1H, quint, J=6.0 Hz), 6.20(1H, s), 6.80(1H, s), 7.32(2H, d, J=8.5 Hz), 7.43(2H, d, J=8.5 Hz)

Preparation 21

To a stirred solution of 3-amino-2-[4-[2-(3-cyano-1-ethyl-5-methyl)pyrrolyl]benzyl]amino-4,6-dimethylpyridine (481 mg) in tetrahydrofuran (5 ml) was added ethyl isothiocyanate (123 μl) and triethylamine (197 μl ) at ambient temperature and the resulting solution was heated at 50° C. for 24 hours.

After cooling, the solvent was removed in vacuo and the volatile materials were removed azeotropically with toluene twice to give 2-[4-[2-(3-Cyano-1-ethyl-5-methyl)pyrrolyl]benzyl]amino-4,6-dimethyl-3-(3-ethyl-thioureido)pyridine (1.34 mmol) as a pale yellow viscous oil.

NMR (CDCl$_3$, $\delta$): 1.12(3H, t, J=7.5 Hz), 1.21 (3H, t, J=7.5 Hz), 2.15(3H, s), 2.30(3H, s), 2.40(3H, s), 3.62(2H, dq, J=7.5 and 8 Hz), 3.87(2H, q, J=7.5 Hz), 4.70(2H, d, J=6 Hz), 5.16(1H, br, t, J=6 Hz), 5.65(1H, m), 6.20(1H, s), 6.42(1H, s), 6.83(1H, br, s), 7.33(2H, d, J=9 Hz), 7.41(2H, d, J=9 Hz)

Preparation 22

A mixture of 2-[4-[2-(3-cyano-1-ethyl-5-methyl)pyrrolyl]benzyl]-amino-4,6-dimethyl-3-(3-ethyl-thioureido)pyridine (1.34 mmol) and iodomethane (250 µl, 4.02 mmol) in acetonitrile (5 ml) was stirred at ambient temperature for 3.5 hrs and then warmed at 50° C. for 4 hours.

The mixture was diluted with ethyl acetate and washed with water and satured brine and dried over anhydrous magnesium sulfate. After filtration, the filtrate was concentrated in vacuo and the resulting solid was washed with diisopropylether. The solid was purified with flash chromatography eluting with methanol-chloroform (3–5% v/v) to afford 3-[4-[2-(3-cyano-1-ethyl -5-methyl)pyrrolyl]benzyl]-5,7-dimethyl-2-ethylamino-imidazo[4,5-b]pyridine (458 mg) as a brown amorphous solid.

NMR (CDCl$_3$, $\delta$): 1.15(3H, t, J=7.5 Hz), 1.20(3H, t, J=7.5 Hz), 2.28(3H, s), 2.53(3H, s), 2.55(3H, s), 3.56(2H, dq, J=7.5 and 6 Hz), 3.83(2H, q, J=7.5 Hz), 3.90(1H, t, J=6 Hz), 5.30(2H, s), 6.20(1H, s), 6.77(1H, s), 7.27(2H, d, J=9 Hz), 7.37(2H, d, J=9 Hz)

EXAMPLE 1

To a mixture of 3-[4-(4-chloro-2-cyano-1-pyrrolyl)-benzyl]-2-ethylthio-7-methyl-3H-imidazo[4,5-b]pyridine (846 mg) in 1,3-dimethyl-2-imidazolidinone (10 ml) was added sodium azide (539 mg) and triethylamine hydrochloride (1.425 g) and stirred at 135° C. for 24 hours. The reaction mixture was poured into ice-water and the pH value was adjusted to 4 with 7% hydrochloric acid, extracted with ethyl acetate (twice) and the organic layer was washed with water, dried over magnesium sulfate and evaporated. The residue was crystallized from methyl cyanide and washed hot methyl cyanide to give 3-[4-[4-chloro-2-(1H-tetrazol-5-yl)-1-pyrrolyl]-benzyl]-2-ethylthio-7-methyl-3H-imidazo[4,5-b]pyridine(766 mg) as a brown solid. mp: 88°–90° C.

NMR (DMSO-d$_6$, $\delta$): 1.40(3H, t, J=7.5 Hz), 2.56(3H, s), 5.43(2H, s), 6.90(1H, d, J=2 Hz), 7.10(1H, d, J=5 Hz), 7.26(4H, br, s), 7.48(1H, d, J=2 Hz), 8.12(1H, d, J=5 Hz)

EXAMPLE 2

3-[4-[4-chloro-2-(1H-tetrazol-5-yl)-1-pyrrolyl]benzyl]2-ethylthio-7-methyl-3H-imidazo[4,5-b]pyridine(50 mg) was dissolved in acqueous in sodium hydroxide solution (0.11 ml), and clarified by sonification. The solution was filtered through a milipor filter. The filtrate was lyophilized to yield sodium salt of 3-[4-[4-chloro-2-(1H-tetrazol-5-yl) -1-pyrrolyl]benzyl]-2-ethylthio-7-methyl-3H-imidazo[4,5-b]pyridine(51.6 mg) as a solid.

NMR (D$_2$O, $\delta$): 1.11(3H, t, J=7.5 Hz), 2.42(3H, s), 3.04(2H, q, J=7.5 Hz), 5.18(2H, s), 6.31(1H, d, J=2 Hz), 6.52–6.65(3H, m), 6.81–6.69(3H, m), 7.90(1H, d, J=5 Hz)

EXAMPLE 3

To a stirred solution of 3-[4-[4-chloro-2-(1H-tetrazol-5-yl)-1-pyrrolyl]benzyl]-2-ethylthio-7-methyl-3H-imidazo[4,5-b]pyridine(700 mg) in dichloromethane(15 ml) was added a solution of m-chloroperbenzoic acid (670 mg; 80% purity) in dichloromethane(15 ml) dropwise below 5° C. and the resulting mixture was stirred for one and half an hour. Another solution of m-chloroperbenzoic acid(67 mg) in dichloromethane(5 ml) was added to the mixture and the stirring was continued for one hour. The mixture was washed with 1N-hydrochloric acid and water. The aqueous layer was extracted with dichloromethane. The organic phase was combined and washed with water. After being dried over anhydrous magnesium sulfate, the solvent was removed in vacuo and the residue was purified by silica gel column chromatography eluting with dichloromethane-methanol (10:1 then 8:1 v/v) to afford 3-[4-[4-chloro-2-(1H-tetrazol-5-yl)-1-pyrrolyl]benzyl]-2-ethylsulfonyl-7-methyl-3H-imidazo[4,5-b]pyridine (210 mg) as a amorphous solid which was powderlized by treating with acetonitrile.

NMR (DMSO-d$_6$, $\delta$): 1.25(3H, t, J=7.5 Hz), 2.67(3H, s), 3.55(2H, q, J=7.5 Hz), 5.86(2H, s), 6.70(1H, d, J=2 Hz), 7.20(2H, d, J=9 Hz), 7.28(2H, d, J=9 Hz), 7.33(1H, d, J=2 Hz), 7.38(1H, d, J=5 Hz), 8.51(1H, d, J=5 Hz)

EXAMPLE 4

To a stirred solution of 3-[4-[4-chloro-2-(1H-tetrazol-5-yl)-1-pyrrolyl]benzyl]-2-ethylsulfonyl-7-methyl-3H-imidazo[4,5-b]pyridine (209 mg) in ethanol(2 ml) was added 1N sodium ethoxide solution in ethanol (1.02 ml) and dichloromethane(30 ml) at room temperature and the resulting mixture was heated under reflux for two hours. After cooling, the mixture was treated with 7% aqueous hydrogenchloric acid and the organic phase was washed with water and dried over anhydrous magnesium sulfute. After filtration the solvent was removed in vauo and the residue was purified by preparative thin layer chromatography eluting with dichloromethane-methanol(8:1 v/v) to give 3-[4-[4-chloro-2-(1H-tetrazol-5-yl)-1-pyrrolyl]benzyl]-2-ethoxy-7-methyl-3H-imidazo[4,5-b]pyridine(97 mg) as a amorphous solid which was powderized by treating with diethylether.

NMR (DMSO-d$_6$, $\delta$): 1.40(3H, t, J=7.5 Hz), 2.46(3H, s), 4.60(2H, q, J=7.5 Hz), 5.21(2H, s), 6.49(1H, d, J=2 Hz), 7.00(1H, d, J=5 Hz), 7.10–7.26(5H, m), 7.99(1H, d, J=5 Hz)

EXAMPLE 5

The following compound was obtained according to a similar manner to that of Example 2.

Sodium salt of 3-[4-[4-chloro-2-(1H-tetrazol-5-yl)-1-pyrrolyl]benzyl]-2-ethoxy-7-methyl-3H-imidazo[4,5-b]pyridine.

NMR (D$_2$O, $\delta$): 1.31(3H, t, J=7.5 Hz), 2.33(3H, s), 4.40(2H, q, J=7.5 Hz), 5.04(2H, s), 6.47(1H, d, J=2 Hz), 6.59(1H, d, J=2 Hz), 6.67(2H, d, J=8 Hz), 6.81(1H, d, J=5 Hz), 7.00(2H, d, J=8 Hz), 7.79(1H, d, J=5 Hz)

EXAMPLE 6

To a stirred solution of 3-[4-(2-bromo-4-cyano-1-methyl-2-pyrrolyl)benzyl]-2-ethylthio-7-methyl-3H-imidazo[4,5-b]pyridine (1.30 g) in xylene (15 ml) was added trimethyltin azide (1.72 g) at 125° C., stirred at the same temperature for 36 hours under nitrogen atmosphere, and the mixture was evaporated in vacuo. The residue was diluted with methanol and conc. hydrochloric acid (1 ml) was added therein. The mixture was stirred for 1 hour at ambient temperature. The mixture was concentrated in vacuo. The residue was diluted with methanol and adjusted to pH4 with aqueous 1N sodium hydroxide. The organic layer was separated, and evaporated in vacuo. The residue was purified by flash column chromatography on silica gel (elution by dichloromethane/methanol=15/1) and by preparative thin layer chromatography (elution by dichloromethane/methanol=8/1) to yield 3-[4-[2-bromo-1-methyl-4-(1H-tetrazol-5yl)-2-pyrrolyl]benzyl-2-ethylthio-7-methyl-3H-imidazo[4,5-b]pyridine (691 mg) as a colorless amorphous solid.

NMR (DMSO-d$_6$, δ): 1.41(3H, t, J=7.5 Hz), 2.56(3H, s), 3.70(3H, s), 5.38(2H, s), 7.08(1H, d, J=5 Hz), 7.20(4H, br, s), 7.62(1H, s), 8.13(1H, d, J=5 Hz)

EXAMPLE 7

To 3-[4-[2-bromo-1-methyl-4-(1H-tetrazol-5-yl)-2-pyrrolyl]benzyl-2-ethylthio-7-methyl-3H-imidazo[4,5-b]pyridine(50 mg) was added 1N aqueous in sodium hydroxide(0.10 ml) and water (1 ml), and the mixture allowed to heat in water bath. The solution was allowed to stand to room temperature, the resulting solid was collected by filtration, and diluted with ethanol. The solution was filtered through a milipor filter. The filtrate was evaporated in vacuo. The residue was dissolved in ethanol(0.2 ml) and water(2.5 ml) and lyophilized to yield sodium salt of 3-[4-[2-bromo-1-methyl-4-(1H-tetrazol-5-yl)-2-pyrrolyl]benzyl-2-ethylthio-7-methyl-3H-imidazo[4,5-b]pyridine (42.6 mg) as a solid.

NMR (DMSO-d$_6$, δ): 1.40(3H, t, J=7.5 Hz), 2.56(3H, s), 3.62(3H, s), 5.34(2H, s), 7.04–7.17(3H, m), 7.19(1H, s), 7.31 (2H, d, J=9 Hz), 8.12(1H, d, J=5 Hz)

EXAMPLE 8

To a mixture of 3-[4-(3-cyano-1-ethyl-5-methyl-2-pyrrolyl)benzyl]-2-ethylthio-7-methyl-3H-imidazo[4,5-b]pyridine (1.52 g) in xylene (15 ml) was added trimethyltin azid (2.26 g) under nitrogen atmosphere, and stirred at 125° C. for 24 hours. The mixture was concentrated in vacuo. To the residue was added methanol and conc. hydrochloric acid (1 ml). The mixture was stirred at ambient temperature for one hour and concentrated in vacuo. The residue was diluted with methanol. The mixture was adjusted to pH4 with 1N sodium hydroxide. The organic layer was separated, and evaporated in vacuo. The residue was purified by flash column chromatography on silica gel (elution by dichloromethane/methanol=15/1) and subsequent crystallization from methyl cyanide to give amorphous powder (1.47 g) of 3-[4-[1-ethyl-5-methyl-3-(1H-tetrazol-5-yl)-2-pyrrolyl]-benzyl]-2-ethylthio-7-methyl-3H-imidazo[4,5-b]pyridine.

NMR (DMSO-d$_6$, δ): 1.01(3H, t, J=7.5 Hz), 1.39(3H, t, J=7.5 Hz), 2.30(3H, s), 2.57(3H, s), 3.72(2H, q, J=7.5 Hz), 5.44(2H, s), 6.33(1H, s), 7.11(1H, d, J=5 Hz), 7.29(4H, br, s), 8.14(1H, d, J=5 Hz)

EXAMPLE 9

The following compound was obtained according to a similar manner to that of Example 2.

Sodium salt of 3-[4-[1-ethyl-5-methyl-3-(1H-tetrazol-5-yl)-2-pyrrolyl]-benzyl]-2-ethylthio-7-methyl-3H-imidazo[4,5-b]pyridine.

NMR (D$_2$O, δ): 0.71(3H, t, J=7.5 Hz), 1.15(3H, t, J=7.5 Hz), 2.16(3H, s), 2.43(3H, s), 3.09(2H, q, J=7.5 Hz), 3.38(2H, q, J=7.5 Hz), 5.34(2H, s), 6.33(1H, s), 6.89–7.02(3H, m), 7.08(2H, d, J=9 Hz), 7.97(1H, d, J=5 Hz)

EXAMPLE 10

To a stirred solution of 3-[4-[1-ethyl-5-methyl-3-(1H-tetrazol-5-yl)-2-pyrrolyl]benzyl]-2-ethylthio-7-methyl-3H-imidazo[4,5-b]pyridine (661 mg) in dichloromethane (15 ml) was added m-chloroperbenzoic acid (778 mg; 80% purity) portionwise in an ice-cooling bath and the resulting mixture was stirred at the same temperature for 2 hours. Then the ice-cooling bath was removed and the mixture was stirred at room temperature for 3 hours. The mixture was diluted with dichloromethane and the organic phase was washed with 10% aqueous sodium hydrogensulfite, water, and brine. After being drying over magnesium sulfate, the organic layer was concentrated in vacuo and the residue was chromatographed on silica gel eluting with 7% methanol-chloroform(v/v) to afford a pale yellow solid. This material was dissolved into dichloromethane and washed with saturated aqueous sodium bicarbonate to give crude 3-[4-[1-ethyl-5-methyl-3-(1H-tetrazol-5-yl)-2-pyrrolyl]benzyl]-2-ethyl-sulfonyl-7-methyl-3H-imidazo[4,5-b]pyridine(305 mg) which was used for the next reaction without further purification.

EXAMPLE 11

A mixture of 3-[4-[1-ethyl-5-methyl-3-(1H-tetrazol-5-yl)-2-pyrrolyl]-benzyl]-2-ethylsulfonyl-7-methyl-3H-imidazo[4,5-b]pyridine (305 mg) and 1.0M sodium ethoxide in ethanol(1.9 ml) in ethanol(3 ml) and dichloromethane (40 ml) was refluxed for one and half an hour. In hydrogen chloride aqueous solution was added to the reaction mixture until the pH of the solution became slightly acidic. The mixture was extracted with dichloromethane, washed with brine, dried over magnesium sulfate was chromatographed on silica gel eluting with 5% methanol-chloroform to obtain 205 mg of the desired compound contaminated with some impurities. This was chromatographed on silica gel eluting with methanol-acetic acid ethyl acetate(1:1:8 v/v) to give 145 mg of the compound which was again contaminated. Preparative thin layer chromatographies were done two times eluting with chloroform-methanol 28% aqueous ammonia(130:25:5 v/v) then ethyl acetate-methanol-acetic acid(1:1:38 v/v) to aftord 2-ethoxy-3-[4-[1-ethyl-5-methyl-3-(1H-tetrazol-5-yl)-2-pyrrolyl]-benzyl[-7-methyl-3H-imidazo[4,5-b]pyridine(72 mg). Crystallization from ether and recrystallization from acetonitrile gave pure compound (32 mg) as a white powder. mp: 192°–196° C.

NMR (DMSO-d$_6$, δ): 1.02(3H, t, J=7.5 Hz), 1.39(3H, t, J=7.5 Hz), 2.29(3H, s) 2.46(3H, s), 3.73(2H, q, J=7.5 Hz), 4.60(2H, q, J=7.5 Hz), 5.28(2H, s), 6.33(1H, s), 7.01(1H, d, J=5 Hz), 7.30(4H, s), 8.01(1H, d, J=5 Hz)

EXAMPLE 12

To a suspension of 2-ethoxy-3-[4-[1-ethyl-5-methyl-3-(1H-tetrazol-5-yl)-2-pyrrolyl]benzyl]-7-methyl-3H-imidazo[4,5-b]pyridine((32.0 ml) in water (1 ml) was added 1N sodium hydroxide(72 µl). The mixture was heated at 90° C. in water bath, clarified by sonication, and lyophilized to yield (30 mg) sodium salt of 2-ethoxy-3-[4-[1-ethyl-5-methyl-3-(1H-tetrazol-5-yl)-2-pyrrolyl]benzyl]-7-methyl-3H-imidazo[4,5-b]pyridine as white powder.

NMR (DMSO-$d_6$, δ): 0.98(3H, t, J=7.5 Hz), 1.40(3H, t, J=7.5 Hz), 2.24(3H, s), 2.44(3H, s), 3.68(2H, q, J=7.5 Hz), 4.60(2H, t, J=7.5 Hz), 5.73(2H, s), 6.10(1H, s), 7.00(1H, d, J=5 Hz), 7.18(2H, d, J=9 Hz), 7.30(2H, d, J=9 Hz), 8.00(1H, d, J=5 Hz)

EXAMPLE 13

A mixture of trimethyltin azide (716 mg) and 3-[4-[1-(2-cyano-5-methyl)pyrrolyl]benzyl]-2-ethoxy-7-methyl-3H-imidazo[4,5-b]pyridine (430 mg) in xylene (5 ml) was stirred at 120° C. for 21 hours. After cooling, the mixture was diluted with ethanol (5 ml), and treated with aqueous 1N sodium hydroxide (3.5 ml), and stirred at ambient temperature for 0.5 hour, and then evaporated in vacuo. The residue was dissolved in ethanol (5 ml), the solution was adjusted to pH5 with 1N hydrochloric acid, organic layer separated, and concentrated in vacuo. The residue was dissolved with 10% methanol-chloroform(50 ml), dried over magnesium sulfate and evaporated in vacuo. The residue was purified by silica gel column chromatography (elution by 3% chloroform) 10% methanol/chloroform and subsequent combined fraction was crystallized from ether to give the first crop of 2-ethoxy-7-methyl-3-[4-[1-(5-methyl-2-1H-tetrazol-5-yl)-1-pyrrolyl]benzyl]-3H-imidazo[4,5-b]pyridine (152 mg) as pale pinky solid. The filtrate was lyophilized with ether-water(1:4) to give the second crop(265 mg). mp: 98°-103 ° C.

NMR (DMSO-$d_6$, δ): 1.48(3H, t, J=7.5 Hz), 1.99(3H, s), 2.48(3H, s), 4.60(2H, q, J=7.5 Hz), 5.29(2H, s), 6.18(1H, d, J=4 Hz), 6.80(1H, d, J=4Hz), 7.01(1H, d, J=5 Hz), 7.21(2H, d, J=9 Hz), 7.31(2H, d, J=9 Hz), 8.01(1H, d, J=5 Hz)

EXAMPLE 14

The following compound was obtained according to a similar manner to that of Example 2

Sodium salt of 2-ethoxy-7-methyl-3-[4-[1-[5-methyl-2-(1H-tetrazol-5-yl)pyrrolyl]benzyl]-3H-imidazo[4,5-b]pyridine.

NMR (D$_2$O, δ): 1.30(3H, t, J=7.5 Hz), 1.73(3H, s), 2.31(3H, s), 4.44(2H, q, J=7.5 Hz), 5.10(2H, s), 6.06(1H, d, J=3 Hz), 6.59(1H, d, J=3 Hz), 6.80(1H, d, J=5 Hz), 6.85(2H, d, J=9 Hz), 7.11(2H, d, J=9 Hz), 7.80(1H, d, J=5 Hz)

Example 15

A solution of 2-ethoxy-7-methyl-3-[4-[5-methyl-2-(1H-tetrazol-5-yl) -1 -pyrrolyl]benzyl]-3H-imidazo [4,5-b]pyridine(108 mg) in 3N hydrochloric acid (0.4 ml) and 1,4-dioxane (1.6 ml) was stirred at 50° C. for 45 min. After cooling, the solvent was removed in vacuo and the residual water was removed azeotropically with 1,4-dioxan. The residue was triturated with acetonitrile and precipitated solid was filtered to give 2-hydroxy-3-[4-[5-methyl-2-(1H-tetrazol-5-yl)pyrrolyl]benzyl]-7-methyl-3H-imidazo[4,5-b]pyridine hydrochloride (87 mg) as a pale brown solid. mp: 168°-174° C.

NMR (DMSO-$d_6$, δ): 2.00(3H, s), 2.34(3H, s), 5.10(2H, s), 6.16(1H, d, J=4 Hz) 6.83(1H, d, J=4 Hz), 6.91(1H, d, J=5 Hz), 7.20(2H, d, J=9 Hz), 7.49(2H, d, J=9 Hz), 7.86(1H, d, J=5 Hz)

EXAMPLE 16

A mixture of trimethyltin azide (284 mg) and 3-[4-[2-(3-cyano-1-ethyl-5-methyl)pyrrolyl]benzyl]-5,7-dimethyl-2-ethoxy-3H-imidazo[4,5-b]-pyridine (114 mg) in xylene (3 ml) was stirred at 125° C. for 16 hours. The reaction mixture was diluted with methanol (5 ml), and to the mixture was added 1N sodium hydroxide (Ca. 2 mg). The mixture was stirred at room temperature for 30 minutes, and then evaporated in vacuo. The residue was dissolved in methanol (5 ml). The solution was adjusted to pH4 with conc. hydrochloric acid and evaporated in vacuo, dried over magnesium sulfate and evaporated in vacuo. The residue was purified by flash column chromatography on silica gel (elution by chloroform then 3% methanol/chloroform). The combined fraction was evaporated in vacuo and was crystallized from added ether. The resulting precipitate was collected by filtiation and washed with methyl cyanide to give 5,7-dimethyl-2-ethoxy-3-[4-[1 -ethyl-5-methyl-3-(1H-tetrazol-5-yl)-2-pyrrolyl]benzyl]-3H-imidazol[4,5-b]pyridine(45 mg) as pale pinky solid. mp: 184°-187° C.

NMR (DMSO-$d_6$, δ): 1.03(3H, t, J=7.5 Hz), 1.36(3H, t, J=7.5 Hz), 2.29(3H, s), 2.43(3H, s), 2.46(3H, s), 3.72(2H, br, q, J=7.5 Hz), 4.56(2H, q, J=7.5 Hz), 5.76(2H, s), 6.33(1H, s), 6.89(1H, s), 7.25(2H, d, J=9 Hz), 7.30(2H, d, J=9 Hz)

EXAMPLE 17

The following compound was obtained according to a similar manner to that of Example 12

Sodium salt of 5,7-dimethyl-2-ethoxy-3-[4-[1-ethyl-5-methyl-3-(1H-tetrazol-5-yl)    -2-pyrrolyl]benzyl]-3H-imidazo[4,5-b]pyridine.

NMR (D$_2$O, δ): 0.63(3H, br, t, J=7.5 Hz), 1.25(3H, t, J=7.5 Hz), 2.11(3H, s), 2.20(3H, s), 2.30(3H, s), 3.32(2H, m), 4.38(2H, q, J=7.5 Hz), 5.11(2H, s), 6.31(1H, s), 6.51(1H, s), 6.98(2H, d, 9 Hz), 7.15(2H, d, J=9 Hz)

EXAMPLE 18

The following compound was obtained according to a similar manner to that of Example 16.

5,7-Dimethyl-3-[4-[1-ethyl-5-methyl-3-(1H-tetrazol-5-yl)-2-pyrrolyl]benzyl]-2-methoxy-3H-imidazo[4,5-b]pyridine. mp: 215°-220° C.

NMR (DMSO-$d_6$, δ): 1.04(3H, t, J=7.5 Hz), 2.29(3H, s), 2.44(3H, s), 2.48(3H, s), 3.71(2H, q, J=7.5 Hz), 4.14(3H, s), 5.29(2H, s), 6.35(1H, s), 6.90(1H, s), 7.26(2H, d, J=9 Hz), 7.30(2H, d, J=9 Hz)

EXAMPLE 19

The following compound was obtained according to a similar manner to that of Example 16.

5,7-Dimethyl-3-[4-[2-[1-ethyl-5-methyl-3-(1H-tetrazol-5-yl)]-pyrrolyl]benzyl]-2-propoxy-3H-imidazo[4,5-b]pyridine. yellow amorphous solid NMR (CDCl$_3$-3 drops CD$_3$OD): 0.99(3H, t, J=7.5 Hz), 1.11(3H, t, J=7.5 Hz), 1.35(2H, m), 2.33(3H, s), 2.54(3H, s), 2.55(3H, s), 3.76(2H, q, J=7.5Hz), 4.53(2H, t, J=7.5 Hz), 5.35(2H, s), 6.50(1H, s), 6.87(1H, s), 7.26(2H, d, J=9 Hz), 7.32(2H, d, J=9 Hz)

EXAMPLE 20

The following compound was obtained according to a similar manner to that of Example 12.

Sodium salt of 5,7-Dimethyl-3-[4-[2-[1-ethyl-5-methyl-3-(1H-tetrazol-5-yl)]pyrrolyl]benzyl]-2-propoxy-3H-imidazo[4,5-b]pyridine. pale yellow powder mp: 162°-166° C.

NMR (DMSO-d$_6$, δ): 0.89(3H, t, J=7.5 Hz), 0.99(3H, t, J=7.5 Hz), 1.75(2H, m), 2.24(3H, s), 2.42(3H, s), 2.48(3H, s), 3.68(2H, m), 4.46(2H, t, J=7.5 Hz), 5.21(2H, s), 6.10(1H, s), 6.86(1H, s), 7.15(2H, d, J=9 Hz), 7.30(1H, d, J=9 Hz)

EXAMPLE 21

The following compound was obtained according to a similar manner to that of Example 16.

5,7-Dimethyl-3-[4-[2-[1-ethyl-5-methyl-3-(1H-tetrazol-5-yl)]-pyrrolyl]benzyl]-2-(2,2,2-trifluoro)ethoxy-3H-imidazo[4,5-b]pyridine. pale yellow amorphous solid NMR (CD3CD, δ): 1.11(3H, t, J=7.5 Hz), 2.33(3H, s), 2.52(3H, s), 2.57(3H, s), 3.70(2H, q, J=7.5 Hz) 4.98(2H, q, J=8 Hz), 5.86(2H, s), 6.63(1H, s), 6.89(1H, s), 7.30(2H, d, J=9 Hz), 7.48(2H, d, J=9 Hz)

EXAMPLE 22

The following compound was obtained according to a similar manner to that of Example 12.

Sodium salt of 5,7-dimethyl-3-[4-[2-[1-ethyl-5-methyl-3-(1H-tetrazol-5-yl)]pyrrolyl]benzyl]-2-(2,2,2-trifluoro)ethoxy-3H-imidazo[4,5-b]pyridine. mp: 162°-172° C.

NMR (DMSO-d$_6$, δ): 0.99(3H, t, J=7.5 Hz), 2.24(3H, s), 2.44(3H, s), 2.52(3H, s), 3.70(2H, q, J=7.5 Hz), 5.26(2H, s), 5.28(2H, q, J=9 Hz), 6.10(1H, s), 6.96(1H, s), 7.19(2H, d, J=9 Hz), 7.33(2H, d, J=9 Hz)

EXAMPLE 23

The following compound was obtained according to a similar manner to that of Example 16.

5,7-Dimethyl-3-[4-[2-[1-ethyl-5-methyl-3-(1H-tetrazol-5-yl)]-pyrrolyl]benzyl]-2-(2-methoxyethoxy)-3H-imidazo[4,5-b]pyridine. pale yellow amorphous NMR (CDCl$_3$, δ): 1.12(3H, t, J=7.5 Hz), 2.32(3H, s), 2.53(3H, s), 2.57(3H, s), 3.31(3H, s), 3.67-3.81(4H, m), 4.67-4.75(2H, m), 5.32(2H, s), 6.62(1H, s), 6.83(1H, s), 7.26(2H, d, J=8.5 Hz), 7.41(2H, d, J=8.5 Hz)

EXAMPLE 24

The following compound was obtained according to a similar manner to that of Example 12.

Sodium salt of 5,7-dimethyl-3-[4-[2-[1-ethyl-5-methyl-3-(1H-tetrazol-5-yl)]pyrrolyl]benzyl]-2-(2-methoxyethoxy)-3H-imidazo[4,5-b]-pyridine. white solid mp: 121°-124° C.

NMR (DMSO-d$_6$, δ): 1.00(3H, J=7.5 Hz), 2.24(3H, s), 2.42(3H, s), 2.47(3H, s), 3.28(3H, s), 3.62-3.77(4H, m), 4.61-4.69(2H, m), 5.21(2H, s), 6.11(1H, s), 6.87(1H, s), 7.20(2H, d, J=8.0 Hz), 7.31(2H, d, J=8.0 Hz)

EXAMPLE 25

The following compound was obtained according to a similar manner to that of Example 16.

5,7-Dimethyl-3-[4-[2-[1-ethyl-5-methyl-3-(1H-tetrazol-5-yl)]-pyrrolyl benzyl]-2-isopropoxy-3H-imidazo[4,5-b]pyridine. pale yellow amorphous NMR (CDCl$_3$, δ): 1.10(3H, t, J=7.5 Hz), 1.42(6H, d, J=6.5 Hz), 2.31(3H, s), 2.52(3H, s), 2.56(3H, s), 3.71(2H, q, J=7.5 Hz), 5.27(2H, s), 5.44(1H, quint, J=6.5 Hz), 6.60(1H, s), 6.81(1H, s), 7.26(2H, d, J=8.5 Hz), 7.41(2H, d, J=8.5 Hz)

EXAMPLE 26

The following compound was obtained according to a similar manner to that of Example 12.

Sodium salt of 5,7-dimethyl-3-[4-[2-[1-ethyl-5-methyl-3-(1H-tetrazol-5-yl)]pyrrolyl]benzyl]-2-isopropoxy-3H-imidazo[4,5-b]pyridine. pale green solid mp: 116°-141° C.

NMR (DMSO-d$_6$, δ): 0.99(3H, t, J=7.5 Hz), 1.36(6H, d, J=6.0 Hz), 2.25(3H, s), 2.41(3H, s), 2.49(3H, s), 3.69(2H, q, J=7.5 Hz), 5.19(2H, s), 5.31(1H, quint, J=6.0 Hz), 6.10(1H, s), 6.86(1H, s), 7.16(2H, d, J=8.0 Hz), 7.31(2H, d, J=8.0 Hz)

EXAMPLE 27

The following compound was obtained according to a similar manner to that of Example 16.

5,7-Dimethyl-3-[4-[2-[1-ethyl-5-methyl-3-(1H-tetrazol-5-yl)]-pyrrolyl]benzyl]-2-ethylamino-3H-imidazo[4,5-b]pyridine. pale yellow powder mp: 237°-243° C.

NMR (DMSO-d$_6$, δ): 1.03(3H, t, J=7.5 Hz), 1.17(3H, t, J=7.5 Hz), 2.29(3H, s), 2.36(3H, s), 2.40(3H, s), 3.24-3.51(2H, m), 3.72(2H, q, J=7.5 Hz), 5.32(2H, s), 6.34(1H, s), 6.70(1H, s), 6.90(1H, br, t, J=5 Hz), 7.19(2H, d, J=9 Hz), 7.29(2H, d, J=9 Hz)

EXAMPLE 28

The following compound was obtained according to a similar manner to that of Example 12.

Sodium salt of 5,7-dimethyl-3-[4-[2-[1-ethyl-5-methyl-3-(1H-tetrazol-5-yl)]pyrrolyl]benzyl]-2-ethylamino-3H-imidazo[4,5-b]pyridine lyophilized solid.

NMR (DMSO-d$_6$, δ): 0.98(3H, t, J=7.5 Hz), 1.17(3H, t, J=7.5 Hz), 2.24(3H, s), 2.36(3H, s), 2.49(3H, s), 3.26-3.50(2H, m), 3.70(2H, q, J=7.5 Hz), 5.26(2H, s), 6.09(1H, s), 6.68(1H, s), 6.89(1H, t, J=6 Hz), 7.08(2H, d, J=9 Hz), 7.29(2H, d, J=9 Hz)

What we claim is:

1. A compound of the formula:

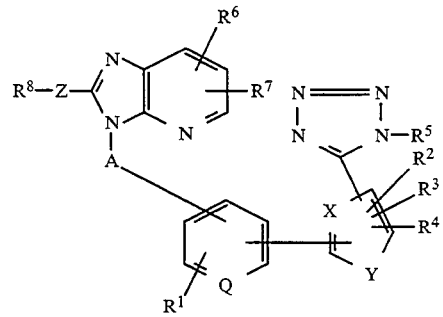

wherein $R^1$ is hydrogen, halogen, nitro, lower alkyl, lower alkoxy, amino or acylamino, $R^2$, $R^3$ and $R^4$ are each hydrogen, halogen, nitro, cyano, lower alkyl, lower alkenyl, lower alkylthio, mono or di or trihalo(lower)alkyl, oxo(lower)alkyl, hydroxy(lower)alkyl or lower alkoxycarbonyl; or $R^2$ and $R^3$ are linked together to form 1,3-butadienylene, R[5] is hydrogen mono-, di- or tri-ar(lower)alkyl, lower alkoxy carbonyl, lower alkane-sulfonyl, or arenesulfonyl, R[6] and R[7] are each hydrogen or lower alkyl, R[8] is hydrogen or lower alkyl which may have a substituent selected from the group consisting of halogen and lower alkoxy, A is lower alkylene, Q is CH or N, X is N or CH, Y is NH, O or S, and Z is NH, S, SO$_2$ or O or a pharmaceutically acceptable salt thereof.

2. A compound of claim 1, wherein

R[1] is hydrogen, halogen, nitro, lower alkyl, lower alkoxy, amino or lower alkanoylamino, R[2], R[3] and R[4] are each hydrogen, halogen, nitro, cyano, lower alkyl, lower alkenyl, lower alkylthio, mono- or di-or trihalo(lower)alkyl, oxo(lower)alkyl, hydroxy(lower)alkyl, carboxy or lower alkoxycarbonyl, R[5] is hydrogen or mono- or di- or triphenyl(lower)alkyl.

3. A compound of claim 2, wherein

R[1] and R[4] are each hydrogen, and

Q and X are each CH.

4. A compound of claim 3, which is represented by the formula:

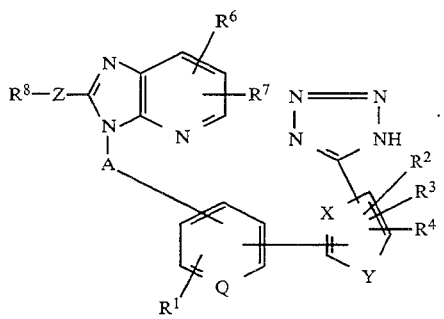

5. A compound of claim 4, wherein the following portion of the formula:

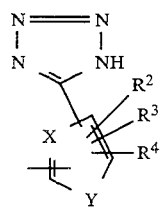

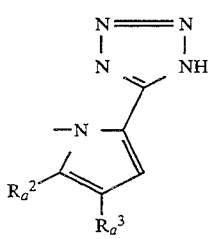

wherein

R$_a^2$ is hydrogen, halogen, cyano, lower alkyl or lower alkylthio, and

R$_a^3$ is hydrogen, halogen, nitro, lower alkyl, lower alkenyl, trihalo(lower)alkyl, oxo(lower)alkyl, hydroxy(lower)alkyl or lower alkoxycarbonyl;

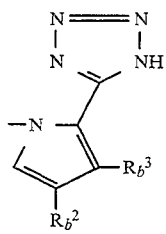

wherein

R$_b^2$ and R$_b^3$ are each halogen;

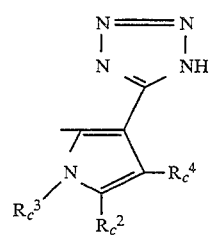

wherein

R$_c^2$ is hydrogen, halogen or lower alkyl,

R$_c^3$ is lower alkyl, and

R$_c^4$ is hydrogen or halogen;

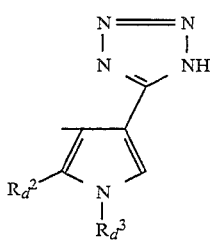

wherein

R$_d^2$ is hydrogen, halogen or lower alkyl, and

R$_d^3$ is lower alkyl;

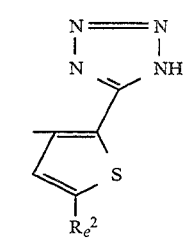

wherein

R$_e^2$ is hydrogen or halogen; or

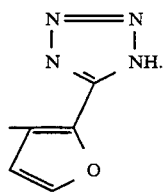

6. A pharmaceutical composition comprising a compound of claim 1 or pharmaceutically acceptable salt thereof in association with a pharmaceutically acceptable, substantially non-toxic carrier or excipient.

7. A method for treating or preventing angiotensin II mediated diseases, which comprises administering a compound of claim 1 or pharmaceutically acceptable salt thereof to human being or animals.

8. A method for treating or preventing hypertension or heart failure, which comprises administering a compound of claim 1 or pharmaceutically acceptable salt thereof to human being or animals.

9. A compound of claim 1 or pharmaceutically acceptable salt thereof for use as a medicament.

10. A compound of claim 1 or pharmaceutically acceptable salt thereof for use as an angiotensin II antagonist.

11. A compound of claim 1, wherein $R^5$ is trityl.

12. A compound of claim 1, wherein $R^5$ is benzyl or benzylhydryl.

13. A compound of claim 5, which is represented by the formula:

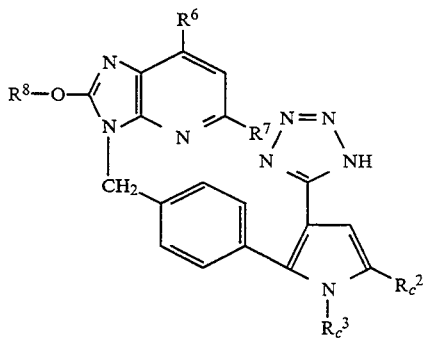

wherein $R^2c$, $R^3c$, $R^6$, $R^7$ and $R^8$ are each lower alkyl.

14. A compound of claim 13, which is 5,7-dimethyl-2-ethoxy-3-[4-[1-ethyl-5-methyl-3-(1H-tetrazol-5-yl)-2-pyrrolyl]benzyl]-3H-imidazo[4,5-b]pyridine or its sodium salt.

* * * * *